United States Patent [19]

Williams

[11] 4,040,123
[45] Aug. 9, 1977

[54] DETACHABLE CONNECTION FOR PIVOTALLY MOUNTING A FACE SHIELD TO A HEAD PROTECTOR

[76] Inventor: Garland S. Williams, 5790 Devonshire Blvd., Miami, Fla. 33155

[21] Appl. No.: 690,393

[22] Filed: May 27, 1976

[51] Int. Cl.² .............................................. A61F 9/06
[52] U.S. Cl. .................................................. 2/10; 2/8
[58] Field of Search ............................. 2/8, 10, 9, 424

[56] References Cited
U.S. PATENT DOCUMENTS

| | | | |
|---|---|---|---|
| 2,447,083 | 8/1948 | Moeller | 2/8 |
| 2,578,171 | 12/1951 | Bub | 2/8 |
| 2,926,357 | 3/1960 | Edwards et al. | 2/8 |
| 3,067,426 | 12/1962 | Tompkins | 2/8 |

*Primary Examiner*—Werner H. Schroeder
*Assistant Examiner*—Peter Nerbun

[57] ABSTRACT

The combination of a protective helmet of rigid material, a face shield, and a connector means for pivotally connecting, supporting and orienting a face shield on the head protective helmet, and which includes resilient means supporting the connector means on the face shield with the connector means normally being engaged in openings in the helmet and which are resiliently and yieldably removable from the openings to detach the shield from the helmet.

5 Claims, 3 Drawing Figures

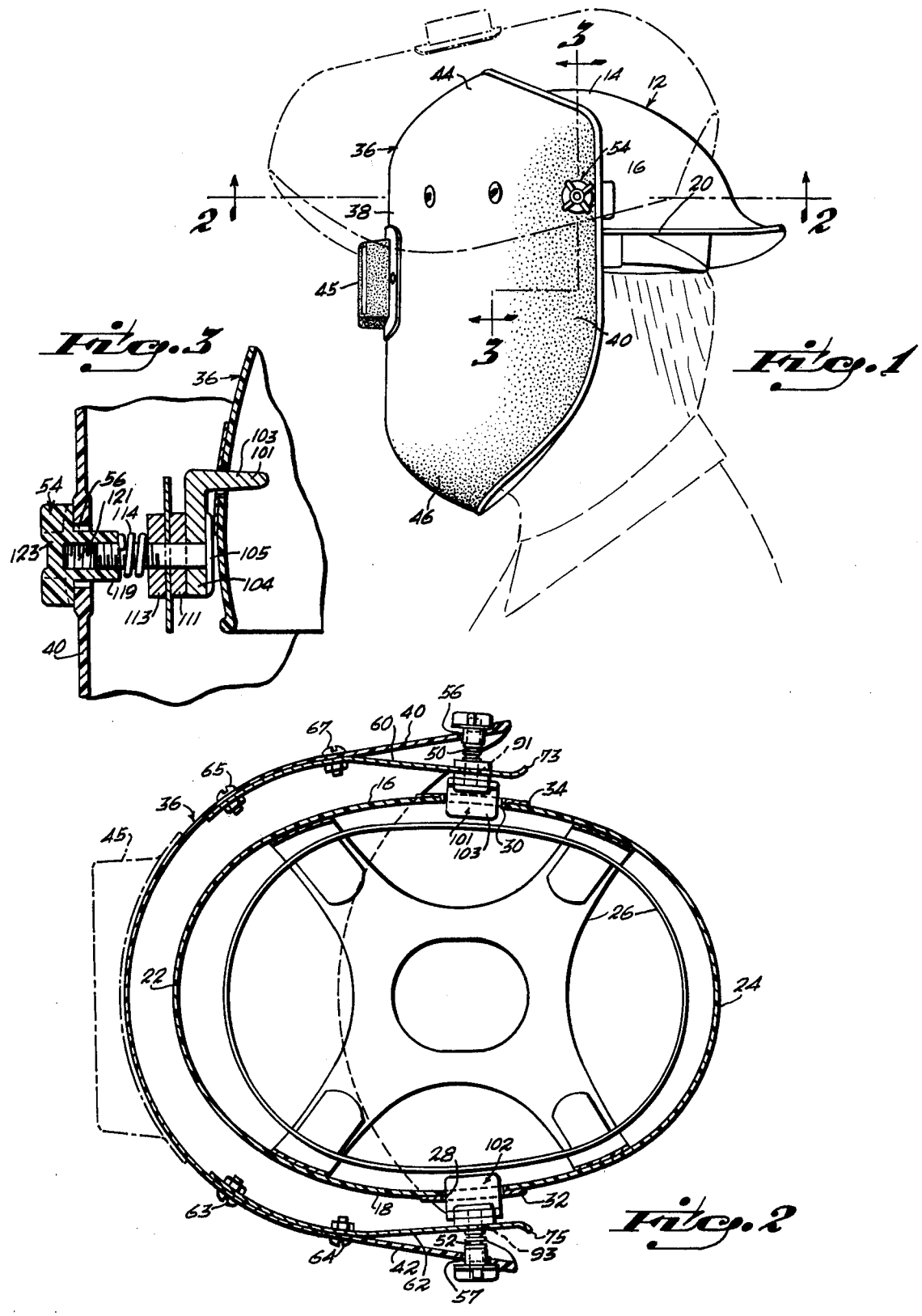

4,040,123

DETACHABLE CONNECTION FOR PIVOTALLY MOUNTING A FACE SHIELD TO A HEAD PROTECTOR

FIELD OF THE INVENTION

This invention relates to rigid head protective devices and face shields, such as are used by welders and, more particularly, to an improved means for mounting a face shield to a rigid helmet which renders the face shield pivotal with respect to the helmet and removable from the helmet.

BACKGROUND OF THE INVENTION

There have been various prior devices which recognize the problem of attaching a face shield to a head protector so that the wearer will find it convenient to use and which may be removed from the heat when not in use. A representative prior art patent is U.S. Pat. No. 2,788,558 which discusses the problems generally in such a combination and discloses a slide permanently affixed to the exterior surface on opposite sides of a head protector and which slides companionately engage a track member on the interior surfaces on opposite sides of a face shield for relatively sliding movement in a seated position. U.S. Pat. No. 3,037,236 discloses a pivotal connector for a face shield and head protector and which provides for removal of the shield; plugs are inserted into slots to affix the shield. U.S. Pat. No. 3,067,426 provides a clutch plate with a swing arm which extends radially from a pivot axis to an arcuate slot defining terminal ends. U.S. Pat. No. 3,114,914 discloses a face shield with strap fasteners to mount to a helmet. U.S. Pat. No. 3,137,005 discloses a welding shield and helmet in which the two are pivotally attached and may be detached and which includes spring hooks to hook up with the lower edge of the helmet. U.S. Pat. No. 3,548,412 discloses a helmet with a bracket to engage a face shield and carries forward the concept of U.S. Pat. No. 3,114,914 and in which the bracket is U-shaped.

It is thus seen that the art has long recognized the problem of detachably connecting a face shield to a head protector or hat so that it is pivotally movable with respect to the hat from an out-of-the-way position above the hat when not in use and into a generally vertical position covering the face when in use. This invention is of an improvement comprising a combination of a hat, face shield and connector means for pivotally connecting the face shield to the hat and orienting the face shield for pivotal movement between a generally vertical orientation and a generally horizontal out-of-the-way orientation, as is described more fully hereinafter.

OBJECTS OF THE PRESENT INVENTION

It is an object of this invention to provide an improved device of the type described in the preceding paragraph for mounting face shields to helmets; wherein a connector means is provided for pivotal movement of the face shield relative to the connector and wherein the connector is secured to the face shield on a resiliently movable leaf spring whereby the leaf spring normally urges the connector means into engagement with the helmet in openings in the sides of the helmet and which is yieldable in response to compressive force between the leaf spring and the face shield to remove the face shield from the helmet.

It is a general object of this invention to provide an improved mounting means for a connector connecting a face shield and a protective helmet together for pivotal movement of the face shield relative to the helmet from an in-use position in which the face shield is generally oriented vertically with respect to the hat and face of a wearer to an out-of-the-way position generally above the head of the wearer.

In accordance with these and other objects which will become apparent hereinafter, the instant invention will now be described with reference to the accompanying drawing in which:

DESCRIPTION OF THE DRAWINGS

FIG. 1 is a side elevation view of the instant invention;

FIG. 2 is a view in cross section taken on the plane indicated by the line 2—2 of FIG. 1 and looking in the direction of the arrows;

FIG. 3 is an enlarged vertical view taken on the plane indicated by the line 3—3 of FIG. 1 and looking in the direction of the arrows.

DESCRIPTION OF THE PREFERRED EMBODIMENT

The numeral 12 generally designates a protective hat, often referred to as a hard hat or, sometimes a bump hat. Generally, such hats include a crown 14 with sides 16 and 18 which extend downwardly terminating at a lower rim 20; and the hat also includes a front 22 and a rear 24. A sweatband 26 is conventionally included in such hats and it is connected to the interior of the hat in a conventional manner. The hat is provided with a pair of slots 28 and 30, one slot on each side of the hat. The slots are not round but, rather, are irregular to key a companionately shaped member inserted into them against rotation relative to the hat. In the preferred embodiment, gromets 32 and 34 are provided to line the slot and the margins of the slot. The openings through the gromets are of predetermined size and shape and, as shown, may be elongated, i.e., have a main longitudinal axis extending from front to rear. The openings are in opposed relation and are arranged generally adjacent the rim.

The face shield is generally designated by the numeral 36 and it includes a generally shell-shaped member with a front face 38 that curves and merges with side faces 40 and 42 and at the top and bottom curves and merges into a dome-shaped partial upper frontal zone 44 and a lower partially cup-shaped zone 46. A conventional window means 45 is centrally located in the front face. The face shield terminates at a periphery which is sized to receive the face of a wearer who is wearing the previously described hard hat between the side faces and upper and lower zones of the shield. Generally, the surface of the rim of the front face of the hat defines a curve as seen in cross section, see FIG. 2, which is foreshortened with respect to the front face and sides of the face shield; and the confronting surfaces are at a predetermined distance from one another in the assembled condition there shown.

Connector means are provided for pivotally connecting and orienting the face shield onto the head protective helmet or hat. To the interior of the face shield above the window level elongate leaf springs 60 and 62 are fixed as by the bolts 63 and 64 and 65 and 67. Each has a forward fixed end and a rearwardly extending rearward end which diverges with respect to the side face of the shield to a terminal end 73 and 75 which is accessible from the rearward portion. A hole is provided in the rearward end of each leaf spring which holes are designated by the numerals 91 and 93. The holes are aligned with one another and they are normally in a projection of holes 56 and 57 which are in the opposing sides of the face shield. These leaf springs are yieldable to a compressive force to move their respective terminal ends toward the inner surface of the face shield with the holes in the leaf springs remaining at all times substantially in the projection of the holes in the face shield, which latter mentioned holes are somewhat larger than the holes in the leaf springs. Pivot pins 50 and 52 extend through the holes of the face shield and leaf spring and terminate at an inner end which is headed and on which there is captivated a key means such as 101 and 102. Reference will now be made to FIG. 3 which illustrates the key means 101 which is the same as 102 with the exception that the upper leg 103 faces inwardly from the opposite side of the face shield. The key means includes a lower leg 104 captivated by the headed end 105 of the pivot pin and it includes a washer 111 and 113 on opposite sides respectively of the leaf spring and a coil spring 114 which urges the washer, sleeve spring and key means against the headed end. The shank of the pivot pin is threaded as shown in FIG. 3 and a headed turning knob 54 with a sleeve-like projection 119 with a threaded recess 121 is provided for threaded engagement with the threaded end of the shank. The operator knob 123 exteriorly of the face shield, which is oversized with respect to the margin of the hole 56 may be utilized to tighten the tension and comprises together with the elements previously mentioned a tension adjusting means for the clamping engagement with the leaf spring and hence a tension means for the pivotal movement of the face shield on the pivot pins while the upper leg or lever 103 which engages in the grommet opening constrains the pivotal movement to the pivotal movement about the pivot pin and hence of the face shield relative to the hat. It is seen that the lever or leg 103 orients the face shield relative to the hat. There has thus been provided a simple tension adjustment means for the pivotal movement of the face shield and an orienting means for the face shield relative to the hat and, additionally, the face shield may be quickly and easily removed by placing one's thumbs behind the face shield and pressing the leaf spring toward the face shield which removes the lever 103 from the grommet opening and, thereafter, the face shield is simply removed from the hat.

What is claimed is:

1. In combination, (a) a rigid head protective helmet, (b) a face shield, and (c) a connector means for pivotally and removably connecting and orienting the face shield onto the head protective helmet,
    A. said helmet being of the type having a crown and a downwardly extending skirt with a front, rear and opposing size zones, and said side zones terminating at a rim at a level above the ears of a wearer's head, said helmet having an elongate opening in each side zone in confronting relation and adjacent the rim,
    B. said face shield having an inner surface and an outer surface and including a front face with a central window means and a rearwardly extending left and right side face each terminating at a generally vertical edge and each side face having a hole of predetermined size adjacent the edge and with their centers defining a line above the central window means,
    C. said connector means comprising:
        a. a first and a second elongate leaf spring each having a first end zone and a second end zone, said first end zone of said first spring being secured to the inner surface of said face shield and said second end zones normally diverging from the adjacent inner surface of the right side face and being of a length to extend beyond the line through the centers of the holes in said side faces, and said second end zone terminating at a terminal end, and said terminal end being accessible at said edge of said right side face, and said second end zone having a hole of a predetermined size smaller than the predetermined size of said hole in said right side face,
        said first end zone of said second leaf spring being secured to the inner surface of said face shield and said second end zone normally diverging from the adjacent inner surface of said left side face and being of a length to extend beyond the line through the centers of the holes in said side faces and said second end zone terminating at a terminal end, and said terminal end being accessible at said edge of said left side face, and said second end zone having a hole of a predetermined size smaller than the predetermined size of said hole in said left side face,
        said holes in said second end zones being aligned with one another and normally within the space comprising a projection of the holes in the side faces of the shield and said second end zones normally converging toward one another;
        said first and second leaf springs being yieldable to a compressive force to move their respective terminal ends toward the inner surface of the right and left side faces respectively of the shield with the holes in each of the second end zones remaining at all times substantially in said projection during relative movement of the leaf springs toward the adjacent inner surface of the face shield,
        b. a first and a second pivot pin each having a headed inner end and a shank terminating at a threaded outer end, and each pin being of a diameter less than that of the holes in said side faces of said shield,
        c. a key means on each pivot pin to constrain the shield to pivotal movement only with respect to the hat while connected thereto, each of said key means comprising a first leg having an inner surface and an outer surface with a hole receiving one of said pivot means and with the inner surface of said first leg in abutting engagement with the adjacent headed inner end; and a second leg extending inwardly from said inner surface to a terminal end, said terminal end of said key means of said first pivot pin being sized and normally extending into the opening in the right side face in a keyed condition, and said terminal end of said key means on said second pivot pin being sized and normally extending into the opening in the left side face in a keyed connection,
        d. means journaling said leaf springs on the shanks of said pivot pins comprising, the shank of said first pivot pin extending through the hole of said first elongate leaf spring and the shank of said second pivot pin extending through the hole of said second elongate leaf spring, said leaf springs normally urging said terminal ends of said second legs into keyed relation in said openings of said helmet, and e. a first keeper exteriorly of said face shield and in abutting engagement with the other surface of said face shield about said hole in the right side face and including an inner sleeve length of a diameter less than that of the hole in said right side face of said shield and having a threaded axial recess in threaded engagement on the threaded end of the first pivot pin, and a first coil spring having an inner end and an outer end about the shank of said first pivot pin and a first pair of washers on the shank of said first pivot pin comprising an inner washer and an outer washer, said inner washer being captivated between the leaf spring and the inner surface of the first leg of the associated key means and said outer washer being captivated between said inner end of said coil spring and said leaf spring, and f. a second keeper exteriorly of said face shield and in abutting engagement with the outer surface of said face shield about said hole in the left side face and including an inner sleeve length of a diameter less than that of the hole in said left side face of said shield and having a threaded axial recess in threaded engagement on the threaded end of the second pivot pin, a second coil spring having an inner end and an outer end about the shank of said second pivot pin and a second pair of washers on the shank of said second pivot pin comprising an inner washer and an outer washer, said inner washer being captivated between the leaf spring and the inner surface of the first leg of the associated key means and said outer washer being captivated between said inner end of said coil spring and said leaf spring.

2. The device as set forth in claim 1 wherein grommet means are included in said hat and line said openings.

3. The device as set forth in claim 2 wherein the openings are elongate, generally oval, and are characterized by a longitudinal front to rear axis which is greater than the vertical axis.

4. The device as set forth in claim 1 wherein the terminal ends of said leaf springs each diverge toward the adjacent surface of the face shield from said second end zones comprising tab means for resiliently moving the distal ends of the leaf springs.

5. The device as set forth in claim 1 wherein the keeper means exteriorly of the face shield comprises a turning knob on the pivot pins.

* * * * *